US00PP27737P3

(12) United States Plant Patent
Booman

(10) Patent No.: US PP27,737 P3
(45) Date of Patent: Feb. 28, 2017

(54) ***SARRACENIA* PLANT NAMED 'WHITE WIZARD'**

(50) Latin Name: ***Sarracenia* hybrid**
Varietal Denomination: White Wizard

(71) Applicant: James Lawrence Booman, Vista, CA (US)

(72) Inventor: James Lawrence Booman, Vista, CA (US)

(73) Assignee: Zantedeschia Lynn Booman, Vista, CA (US)

( * ) Notice: Subject to any disclaimer, the term of this patent is extended or adjusted under 35 U.S.C. 154(b) by 127 days.

(21) Appl. No.: 14/544,495

(22) Filed: Jan. 13, 2015

(65) Prior Publication Data
US 2016/0205861 P1 Jul. 14, 2016

(51) Int. Cl.
*A01H 5/00* (2006.01)

(52) U.S. Cl.
USPC ..... Plt./477

(58) Field of Classification Search
USPC ..... Plt./477
See application file for complete search history.

*Primary Examiner* — Keith Robinson

(57) ABSTRACT

A new cultivar of *Sarracenia* plant named 'White Wizard' that is characterized by long tubular shaped leaves with a vertical hood extending above the leaf opening, green leaves with red veins and a red-brown colored lip, white translucent chlorophyll free patches near the hood margins and the leaf opening and wavy hood margins.

1 Drawing Sheet

Botanical classification: *Sarracenia* hybrid.
Variety denomination: 'WHITE WIZARD'.

BACKGROUND OF THE INVENTION

The present invention relates to a new and distinct cultivar of *Sarracenia* plant botanically known as *Sarracenia* hybrid and hereinafter referred to by the cultivar name 'White Wizard'.

The new *Sarracenia* plant is the product of a breeding program conducted by the inventor in Vista, Calif. The objective of the breeding program is to create new ornamental carnivorous pitcher plants with large leaves, high leaf counts and distinctive leaf colors 'White Wizard' originated from the crossing of a large number of unidentified proprietary selections of *Sarracenia* hybrid (not patented) in 2009. The exact parent plants are unknown. The resulting seeds were subsequently harvested and grown. 'White Wizard' was selected as a single plant within the progeny of the stated cross in a controlled environment in Vista, Calif. in 2009.

Asexual reproduction of the new cultivar 'White Wizard' first occurred by tissue culture in 2011 in Rancho Santa Fe, Calif. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Sarracenia* cultivar 'White Wizard'. These traits in combination distinguish 'White Wizard' as a new and distinct cultivar apart from other existing known varieties of *Sarracenia*.

1. *Sarracenia* 'White Wizard' exhibits long tubular shaped leaves with a vertical hood extending above the leaf opening.
2. *Sarracenia* 'White Wizard' exhibits green leaves with red veins and a red-brown colored peristome.
3. *Sarracenia* 'White Wizard' exhibits leaves with white translucent chlorophyll free patches near the hood margins and near the leaf opening.
4. *Sarracenia* 'White Wizard' exhibits wavy hood margins.
5. *Sarracenia* 'White Wizard' exhibits a hemispherical hood shape.

'White Wizard' can be compared to plants of an unidentified selection of *Sarracenia purpurea*. In side-by-side comparisons conducted by the inventor in Vista, Calif., plants of the new *Sarracenia* differed from plants of the unidentified selection of *Sarracenia purpurea* in the following characteristics:

1. *Sarracenia* 'White Wizard' exhibits longer leaves than the leaves of the unidentified selection of *Sarracenia purpurea*.
2. *Sarracenia* 'White Wizard' exhibits white translucent chlorophyll free patches near the hood margins and near the leaf opening. The unidentified selection of *Sarracenia purpurea* does not have any white translucent patches.
3. *Sarracenia* 'White Wizard' exhibits leaf hood margins that are more wavy and undulating than the leaf hood margins of the unidentified selection of *Sarracenia purpurea*.
4. *Sarracenia* 'White Wizard' exhibits a hemispherical shaped hood. The unidentified selection of *Sarracenia purpurea* has drooping earlobe shaped portions on each side of the hood.

'White Wizard' can be compared to plants of an unidentified selection of *Sarracenia leucophylla*. In side-by-side comparisons conducted by the inventor in Vista, Calif., plants of the new *Sarracenia* differed from plants of the unidentified selection of *Sarracenia leucophylla* in the following characteristics:

1. *Sarracenia* 'White Wizard' exhibits a vertical leaf hood. The leaf hood of the unidentified selection of *Sarracenia leucophylla* curves over the leaf opening.
2. *Sarracenia* 'White Wizard' exhibits white translucent chlorophyll free patches near the hood margins and near the leaf opening. The unidentified selection of *Sarracenia leucophylla* has white translucent chlorophyll free areas covering most of the hood and the top of the leaf in the summer.
3. *Sarracenia* 'White Wizard' exhibits a wider leaf hood with more and wider undulations in the top leaf margins than the leaf hood of the unidentified selection of *Sarracenia leucophylla.*
4. *Sarracenia* 'White Wizard' exhibits hollow tube shaped leaves through the growing season. The leaves of the unidentified selection of *Sarracenia leucophylla* are flat in the spring developing into hollow tube shaped leaves in the summer.

*Sarracenia* 'White Wizard' can be compared to *Sarracenia* 'Cobra Nest' (U.S. Plant Pat. No. 12,821). 'White Wizard' is different than 'Cobra Nest' in the following characteristics:

1. 'White Wizard' exhibits a smaller number of leaves than the number of leaves of 'Cobra Nest'.
2. 'White Wizard' exhibits longer leaves than the leaves of 'Cobra Nest'.

BRIEF DESCRIPTION OF THE DRAWING

The accompanying photograph illustrates the distinguishing traits of *Sarracenia* 'White Wizard'. The plant in the photograph shows an overall view of a 24 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Sarracenia* cultivar named 'White Wizard'. Data was collected in Vista, Calif. from 24 month old plants grown in a polyethylene greenhouse in 10 cm. diameter containers. The time of year was autumn and the temperature range was 26-40 degrees Centigrade during the day and 18-22 degrees Centigrade at night. The light level was 3000 foot candles. No photoperiodic treatments were used. Color determinations are in accordance with The Royal Horticultural Society Colour Chart 2007 edition, except where general color terms of ordinary dictionary significance are used. The growing requirements are similar to the species. 'White Wizard' has not been tested under all possible conditions and phenotypic differences may be observed with variations in environmental, climatic, and cultural conditions, however, without any variance in genotype.

Botanical classification: *Sarracenia* hybrid 'White Wizard'.

Parentage: 'White Wizard' originated from a cross of two unidentified proprietary selections of *Sarracenia* hybrid.

Propagation: Tissue culture.

Time to initiate roots on a tissue-culture plantlet: About 30 days at 20 degrees Centigrade.

Time to produce a rooted tissue-cultured plantlet: About 150 days at 20 degrees Centigrade.

Crop time: Approximately 18 months.

Temperature tolerance: 0 to 40 degrees Centigrade.

Annual or perennial: Perennial.

Root description: Central root with sparse side roots 1 mm. in diameter, initially 155C in color, maturing to 175D.

Plant shape: Upright carnivorous perennial plant with erect tubular leaves.

Plant growth habit: Compact; upright with strong leaves; leaves arise in a spiral from a rhizome tip; vigorous growth.

Containers: 10 cm. containers.

Plant height: Soil level to top of leaves 13.9 cm.

Plant width: 14.6 cm.

Foliage description:

*Leaf shape.*—Tubular to trumpet-shaped, smaller diameter at base and larger diameter at apex with peristome at opening; mostly erect to slightly leaning; keel on one side of leaf; large terminal hood; sessile.

*Hood shape.*—Hemispherical in shape; apex rounded; margin entire, wavy and undulating.

*Number of leaves per plant.*—8-10.

*Leaf length.*—13.9 cm.

*Leaf diameter.*—2.6 cm. at apex and 6 mm. at base.

*Leaf texture (both surfaces).*—Velvety with fine pubescence.

*Keel length.*—9.6 cm.

*Keel width.*—6 mm.

*Hood length.*—3.8 cm.

*Hood width.*—5.7 cm.

*Hood texture.*—Outer surface velvety with fine pubescence and inner surface covered with downward pointing hyaline hairs 1-2 mm. in length.

*Peristome dimensions.*—3 mm. in width at hood, 7 mm. in width at front.

*Peristome texture.*—Glabrous.

*Peristome color.*—185B.

*Young leaf color outer surface.*—145C, veins on upper half of leaf 53B; hood color 145C.

*Young leaf color inner surface.*—145C; hood color 145C.

*Mature leaf color outer surface.*—144B, veins on upper half of leaf 185A, upper 2 cm. speckled N155A; hood color 144B with veins 185A and speckled N155A toward margins.

*Mature leaf color inner surface.*—144B, upper 2 cm. speckled N155A; hood color 144B with veins 185A and speckled N155A toward margins.

Flower: 'White Wizard' has not produced flowers to date.

Fruit and seed: 'White Wizard' has not produced fruit or seed to date.

Disease and pest resistance: Plants of the new *Sarracenia* exhibit good resistance to fungal diseases including *Botrytis cinerea* and *Colletotrichum gloeosporioides*. Mature plants are susceptible to mealy bugs (*Myzus persicae*) on the rhizome. Young leaves susceptible to green peach aphids (*Pseudococcus longispinus*). Mature leaves not susceptible to green peach aphids.

The invention claimed is:

1. A new and distinct variety of *Sarracenia* plant named 'White Wizard' as described and illustrated.

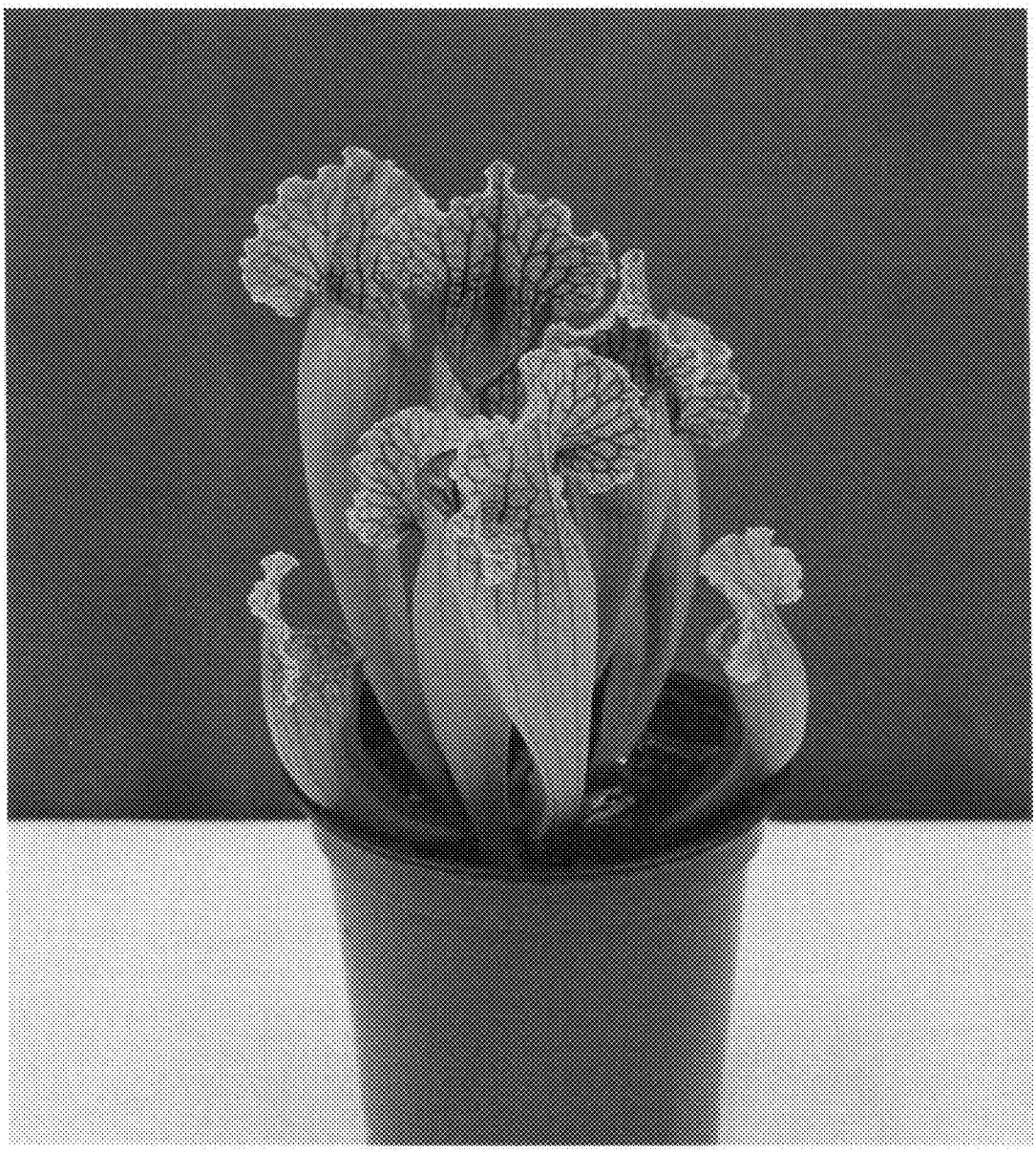

* * * * *